United States Patent
Geimer

(10) Patent No.: US 10,004,754 B2
(45) Date of Patent: Jun. 26, 2018

(54) ANP FRAGMENT ADJUVANT THERAPY TO STANDARD OF CARE (SOC) DIURETIC TREATMENT

(71) Applicant: MADELEINE PHARMACEUTICALS PTY LTD, Mount Barker (AU)

(72) Inventor: Thomas Robert Geimer, Emu Bay (AU)

(73) Assignee: Madeleine Pharmaceuticals Pty Ltd., Mount Barker (AU)

( * ) Notice: Subject to any disclaimer, the term of this patent is extended or adjusted under 35 U.S.C. 154(b) by 0 days. days.

(21) Appl. No.: 15/124,804

(22) PCT Filed: Mar. 13, 2015

(86) PCT No.: PCT/AU2015/000142
§ 371 (c)(1),
(2) Date: Sep. 9, 2016

(87) PCT Pub. No.: WO2015/135024
PCT Pub. Date: Sep. 17, 2015

(65) Prior Publication Data
US 2017/0020899 A1    Jan. 26, 2017

(30) Foreign Application Priority Data

Mar. 14, 2014 (WO) ................ PCT/AU2014/000256
Apr. 9, 2014 (AU) ................................ 2014901300

(51) Int. Cl.
| | |
|---|---|
| A61K 38/22 | (2006.01) |
| A61P 9/08 | (2006.01) |
| A61P 13/12 | (2006.01) |
| A61K 31/341 | (2006.01) |
| A61K 31/635 | (2006.01) |
| A61K 31/585 | (2006.01) |
| A61K 45/06 | (2006.01) |
| A61K 31/197 | (2006.01) |
| C07K 14/58 | (2006.01) |

(52) U.S. Cl.
CPC .......... *A61K 31/635* (2013.01); *A61K 31/197* (2013.01); *A61K 31/341* (2013.01); *A61K 31/585* (2013.01); *A61K 38/2221* (2013.01); *A61K 38/2242* (2013.01); *A61K 45/06* (2013.01); *A61P 9/08* (2018.01); *A61P 13/12* (2018.01); *C07K 14/58* (2013.01)

(58) Field of Classification Search
None
See application file for complete search history.

(56) References Cited

U.S. PATENT DOCUMENTS 5,691,310 A    11/1997  Vesely
2005/0113286 A1    5/2005  Schreiner et al.
2007/0141634 A1    6/2007  Wuolteenaho et al.
2009/0062730 A1    3/2009  Woo
2012/0277155 A1    11/2012  VanAntwerp et al.
2016/0051631 A1    2/2016  Geimer et al.

FOREIGN PATENT DOCUMENTS

| WO | WO 2007/130672 | 11/2007 |
| WO | WO 2009/040031 | 4/2009 |
| WO | WO 2012/019237 A1 | 8/2011 |
| WO | WO 2012/115771 | 8/2012 |
| WO | WO 2012/115772 | 8/2012 |
| WO | WO 2013/154784 A1 | 10/2013 |
| WO | WO 2014/138796 | 9/2014 |

OTHER PUBLICATIONS

Koniari et al, 2011. International Journal of Nephrology, pp. 1-10.*
GenBank accession XP_001141705.1 (Oct. 25, 2012).
Lenz et al. "Cardiac hormones eliminate some human squamous lung carcinomas in athymic mice," European Journal of Clinical Investigation, Mar. 2010, vol. 40, No. 3, pp. 242-249.
Saito et al. "Clinical application of atrial natriuretic polypeptide in patients with congestive heart failure: beneficial effects on left ventricular function," Circulation, vol. 76, No. 1, pp. 115-124 (Jul. 1987).
Vesely "Which of the Cardiac Natriuretic Peptides Is Most Effective for the Treatment of Congestive Heart Failure, Renal Failure and Cancer?" Clinical and Experimental Pharmacology and Physiology, Mar. 2006, vol. 33, No. 3, pp. 169-176.
International Search Report and Written Opinion prepared by the Australian Patent Office dated Jun. 25, 2015, for International Application No. PCT/AU2015/000142.
Vesely L D et al., "Comparison of vessel dilator and long-acting natriuretic peptide in the treatment of congestive heart failure", American Heart Journal, 1999, vol. 138, No. 4, Part 1, pp. 625-632.
Vesely L D et al. "Vessel Dilator Enchances Sodium and Water Excretion and Has Beneficial Hemodynamic Effects in Persons With Congestive Heart Failure", Circulation, 1998, vol. 98, pp. 323-329.
Patel H et al. "Combined Treatment with Vessel Dilator and Kaliuretic Hormone in Persons with Congestive Heart Failure", Exp Biol Med, 2004, vol. 229, pp. 521-527.
Bonios M J et al., "The challenge of treating congestion in advanced heart failure", Expert Rev Cardiovasc. Ther., (2011), vol. 9, No. 9, pp. 1181-1191.
Teerlink J R et al., "Serelaxin, recombinant human relaxin-2, for treatment of acute heart failure (RELAX-AHF): a randomized, placebo-controlled trial", Lancet, (Jan. 2013), vol. 381, pp. 29-39.
Vardeny O. et al , "First-in-Class Angiotensin Receptor Neprilysin Inhibitor in Heart Failure", Clinical Pharmacology & Therapeutics, (Oct. 2013), vol. 94, No. 4, pp. 445-448.

(Continued)

*Primary Examiner* — Zachary Howard
(74) *Attorney, Agent, or Firm* — Sheridan Ross P.C.

(57) ABSTRACT

A therapeutic method for treating and/or preventing diseases and medical conditions typically treated by administering diuretic agents (eg congestive heart failure). The method may comprise, for example, administering to a subject a diuretic agent in combination with vessel dilator (VSDL) or a variant or modified peptide thereof. The administration of the diuretic agent may be a component of a standard of care (SOC) treatment.

13 Claims, 7 Drawing Sheets

(56) References Cited

OTHER PUBLICATIONS

Vesely D L et al., "Three Peptides From the Atrial Natriuretic Factor Prohormone Amino Terminus Lower Blood Pressure and Produce Diuresis, Natriuresis, and/or Kaliuresis in Humans", Circulation, vol. 90, No. 3, Sep. 1994, pp. 1129-1140.

Serafino et al. "Atrial Natriuretic Peptide: A Magic Bullet for Cancer Therapy Targeting Wnt Signaling and Cellular pH Regulators," Current Medicinal Chemistry, Jul. 2014, vol. 21, pp. 2401-2409.

Extended Search Report for European Patent Application No. 15761744.0, dated Nov. 3, 2017, 10 pages.

"Glomerular Filtration Rate (GFR)," National Kidney Foundation, 2015, 4 pages.

\* cited by examiner

ANP FRAGMENT ADJUVANT THERAPY TO STANDARD OF CARE (SOC) DIURETIC TREATMENT

CROSS REFERENCE TO RELATED APPLICATIONS

This application is a national stage application under 35 U.S.C. 371 and claims the benefit of PCT Application No. PCT/AU2015/000142 having an international filing date of 13 Mar. 2015, which designated the United States, which PCT application claimed the benefit of International Application No. PCT/AU2014/000256 filed on 14 Mar. 2014, and Australian Patent Application No. 2014901300 filed 9 Apr. 2014, the disclosure of which are incorporated herein by reference in their entirety.

TECHNICAL FIELD

The present invention relates to a novel therapeutic method for treating and/or preventing diseases and medical conditions typically treated by administering diuretic agents.

INCORPORATION BY REFERENCE

The following patent and patent applications are referred to in the following description:
U.S. Pat. No. 5,691,310 titled "Methods of treatment using proANF peptides";
PCT/AU2011/001026 (WO 2012/019237) titled "Therapeutic method for treating congestive heart failure" and filed on 11 Aug. 2011; and
PCT/AU2014/000256 (WO 2014/138796) titled "Dosage regimen for therapeutic method" and filed on 14 Mar. 2014. Their content is hereby incorporated by reference in their entirety.

BACKGROUND

Diuretic agents are a class of drugs that increase urine production, thereby leading to increased urine volume. There are several different types of diuretics that act in distinct ways. The main types are osmotic diuretics (eg mannitol), high ceiling diuretics such as furosemide, bumetanide, ethacrynic acid and torsemide (also known as loop diuretics), thiazides (eg hydrochlorothiazide), carbonic anhydrase inhibitors (eg acetazolamide), and potassium-sparing diuretics (eg aldosterone antagonists such as spironolactone, and epithelial sodium channel blockers such as amiloride). Diuretic agents are used in the treatment and/or prevention of a wide variety of diseases and medical conditions including, for example, liver cirrhosis, ascites associated with liver cirrhosis, diabetes insipidus, glaucoma, and renal diseases and conditions such as nephrotic syndrome, hypercalcemia, contrast-induced nephropathy (CIN), chronic kidney disease (CKD) (including CKD in patients on dialysis) and acute renal failure (ARF) (as may be associated with cardiovascular operations, severe traumatic injury and haemolytic transfusion reactions) which is otherwise known as acute kidney injury (AKI). However, the greatest use of diuretic agents resides in the treatment of oedema associated with hypertension, cardio-renal syndrome (CRS) and congestive heart failure (both chronic congestive heart failure (CHF) and acute decompensated congestive heart failure (ADCHF; also abbreviated to ADHF)).

Indeed, the administration of diuretic agents is a critical component of the typical treatments or "standard of care" (SOC) treatments of CHF patients, and in many cases, such treatments comprise the long term use of diuretic agents (usually a loop diuretic). Generally, the aim of these treatments is to achieve an increase in urine output and weight reduction of 0.5 to 1.0 kg daily (Heart Foundation Guidelines, October 2011), at which time the dosage of the diuretic agent ought to be reduced (albeit with ongoing regular reassessment and dosage adjustment according to volume status, if necessary). However, even with dosage reduction, long term use of diuretic agents may be undesirable or cause complications. For instance, during treatment with loop diuretics, patients should be monitored for hypokalaemia (a condition wherein there are abnormally low amounts of potassium in the blood which can lead to a range of symptoms and other undesirable outcomes including cardiac arrhythmias, constipation, and muscle weakness, myalgia and cramps (Heart Foundation Guidelines, October 2011)). The use of the loop diuretic furosemide has been described as "entrenched in today's suggested standard of care for chronic cardiac failure" (Weber, 2004). Integral to the safe long term use of this agent in CHF patients is the regular monitoring of serum electrolytes to manage, not only for incidents or risk of hypokalaemia, but also hypomagnesemia (a condition characterised by low amounts of magnesium in the blood and capable of causing symptoms such as cardiac arrhythmias and tachycardia, hypertension, muscle weakness and cramps, tremors, confusion and depression), and hypercalcemia (a condition characterised by an abnormally high blood concentration of calcium and capable of causing symptoms such as fatigue, bone pain, abdominal pain, muscle weakness, vomiting and constipation). In addition, furosemide can lead to a thiamine deficiency (Weber 2004), which if left untreated (eg by supplemental dietary thiamine) may cause symptoms of fatigue, irritability, depression and abdominal discomfort. Furosemide use has also been linked to hyperglycaemia and the development of gout caused by hyperuricemia. Moreover, it has been recognised that with oral administration (generally the desired mode for long term, at home use of drug agents) of diuretic agents, a "vicious cycle" can develop where the deteriorating clinical status of the patient contributes to gut wall oedema which, in turn, can cause reduced absorption of the diuretic agent, less effective fluid loss and, consequently, further deterioration in the patient's condition (Heart Foundation Guidelines, October 2011).

Since SOC treatments of CHF patients critically involves the administration of a diuretic agent, it is unremarkable that renal function is a key factor in predicting the risk of rehospitalisation and mortality in patients with CHF, as well as in limiting the management of patients with ADCHF. As such, patients with impaired cardiac and renal function are often described as a separate entity (ie as patients with cardio-renal syndrome, CRS), and provide a greater societal burden in terms of health care costs, morbidity and mortality. Given then that CHF/ADCHF patients commonly show diuretic resistance and that SOC treatments may, in some patients, actually lead to a reduced level of responsiveness to diuretic therapy (eg by the development of acute diuretic resistance or refractory diuretic responsiveness; Valente et al., 2014, and Voors et al., 2014), which is commonly addressed by simply increasing the dosage of the diuretic agent until a maximum effective dose is reached (ie. where there is no further diuresis achieved), treatments that target this patient population are specifically lacking and an unmet clinical need exists.

Thus, there is a desire in the art to avoid long term use of any one diuretic agent (such as furosemide) or, otherwise, at least reduce the dosage level(s) of the diuretic agent during such long term usage, as well as improve treatment options for CHF patients and ADCHF patients and, particularly in those patients showing impaired renal function.

The present applicant is developing novel therapies for, inter alia, CHF and ADCHF involving, in particular, the administration of vessel dilator (VSDL/VD). VSDL is a naturally occurring 37 amino acid cardiac peptide consisting of amino acids 31-67 of the 126 amino acid protein known as atrial natriuretic peptide (ANP) prohormone (proANP) (Vesely, 2002). The main biological activity of VSDL is to regulate blood pressure and maintain plasma volume in healthy individuals (Vesely, 2003). It is considered that VSDL offers a safe and potential effective treatment for conditions such as CHF and ADCHF by mediating beneficial haemodynamic effects through mechanisms of regulating plasma volume and blood pressure (BP) within clinically acceptable ranges and without seriously adverse side-effects (Vesely et al., 1994 and 1998). Indeed, in previous work (described in WO 2012/019237) using intravenous (iv) infusion of VSDL in patients showing either acute exacerbations of chronic CHF or ADCHF, the present applicant was able to achieve improved outcomes (eg increased cardiac index (CI), and drops in pulmonary capillary wedge pressure (PCWP) and blood pressure) without side-effects, even with very low doses of the peptide. However, it was hitherto considered that these beneficial haemodynamic effects are achieved primarily through vasodilatory activity. In further work described herein, it has been found that infusion of VSDL (along with SOC treatment) can achieve significant improvements in renal function and increased urine output associated with improvements in cardiac function, even in patients showing renal impairment (eg as shown by an estimated glomerular filtration rate (eGFR) of <75-90 ml/min/1.73 m$^2$). As a consequence, it is considered that VSDL shows considerable promise as the basis of an adjuvant treatment to standard of care (SOC) diuretic treatment of CHF and/or ADCHF patients.

SUMMARY

According to a first aspect, there is provided a method for treating and/or preventing a disease or medical condition in a subject, comprising administering to the subject a diuretic agent in combination with a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof).

The method of the invention may be used for treating and/or preventing any disease or medical condition typically treated by administering a diuretic agent or, in other words, any disease or medical condition where diuresis is desired.

The method of the invention may be particularly well suited to the treatment of subjects showing impaired kidney function or acute diuretic resistance, or who otherwise develop refractory diuretic responsiveness (eg after prolonged use and/or elevated dosing of diuretic agents).

In one embodiment of the method of the invention, the administration of the diuretic agent comprises standard of care (SOC) treatment for the disease or medical condition.

In a second aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) in the preparation of a medicament for treating and/or preventing a disease or medical condition in a subject, wherein the peptide (or variant or modified peptide thereof) is administered in combination with a diuretic agent.

In a third aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) for treating and/or preventing a disease or medical condition in a subject, wherein the peptide (or a variant or modified peptide thereof) is administered in combination with a diuretic agent.

In a fourth aspect, the present invention provides a kit comprising a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) and a diuretic agent optionally with instructions for the use of said kit in a method for treating and/or preventing a disease or medical condition in a subject.

In a fifth aspect, the present invention provides a method for treating and/or preventing a disease or medical condition in a subject, comprising administering to the subject a vasodilator agent in combination with a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof).

In a sixth aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) in the preparation of a medicament for treating and/or preventing a disease or medical condition in a subject, wherein the peptide (or variant or modified peptide thereof) is administered in combination with a vasodilator agent.

In a seventh aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) for treating and/or preventing a disease or medical condition in a subject, wherein the peptide (or a variant or modified peptide thereof) is administered in combination with a vasodilator agent.

In an eighth aspect, the present invention provides a kit comprising a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) and a vasodilator agent optionally with instructions for the use of said kit in a method for treating and/or preventing a disease or medical condition in a subject.

In a ninth aspect, the present invention provides a kit comprising vessel dilator (VSDL) (or a variant or modified peptide thereof) and a natriuretic peptide such as any active peptide fragment from within the C-terminal amino acids 94-126 of atrial natriureic peptide prohonnone (proANP) such as ANP (or a variant or modified peptide thereof) and urodilatin (or a variant or modified peptide thereof), BNP (or a variant or modified peptide thereof) or a chimaeric form of such natriuretic peptides (for example, those including CNP and/or DNP), optionally with instructions for the use of said kit in a method for treating CHF.

In a tenth aspect, the present invention provides a kit comprising vessel dilator (VSDL) (or a variant or modified peptide thereof) and a vasodilator agent such as relaxin optionally with instructions for the use of said kit in a method for treating CHF or ADCHF.

In an eleventh aspect, the present invention provides a kit comprising vessel dilator (VSDL) (or a variant or modified peptide thereof), a vasodilator agent such as relaxin and a neprilysin inhibitor such as sacubitril (AHU-377), optionally with instructions for the use of said kit in a method for treating CHF or ADCHF.

BRIEF DESCRIPTION OF FIGURES

FIG. 5A. systolic blood pressure, and FIG. 5B. diastolic blood pressure.

DETAILED DESCRIPTION

Figure 1:
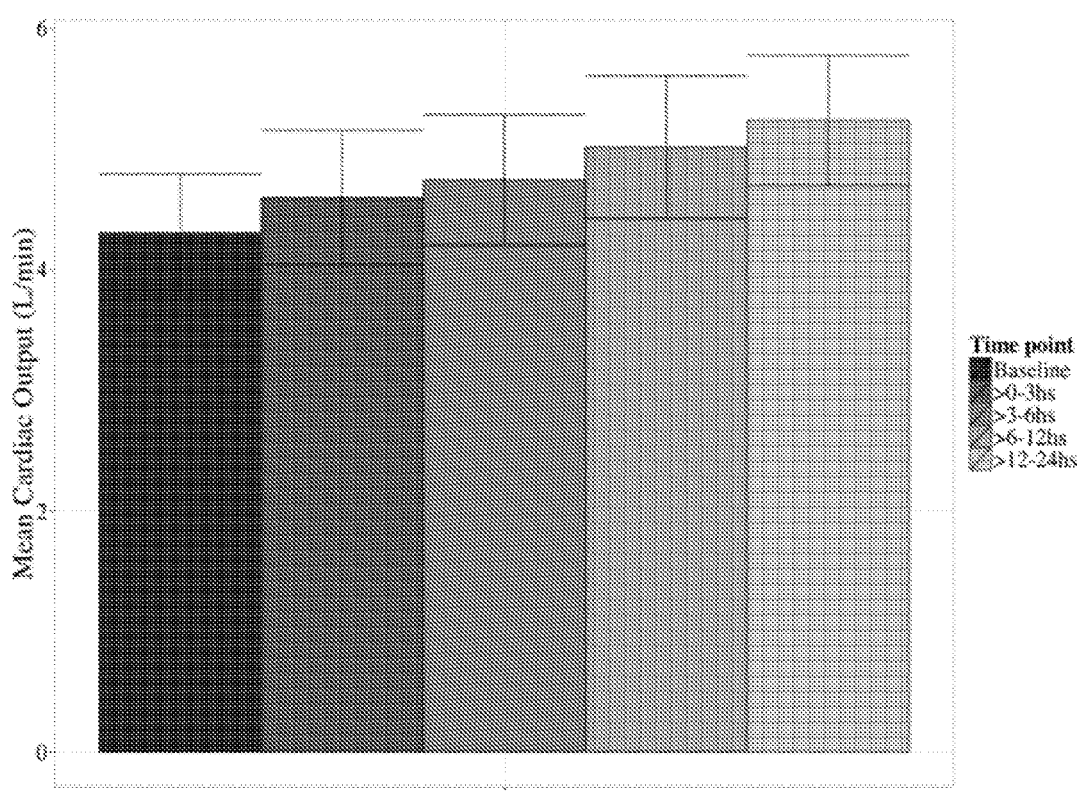
FIG. 1 shows a plot of Mean Cardiac Output in stable CHF patients treated with SOC treatment and VSDL over time.

Congestive heart failure (CHF) is characterised by the inability of the heart to pump blood forward at a sufficient rate to meet the metabolic demands of the body or the ability to do so only if the cardiac filling pressures are abnormally high, or both (Lilly, 2003). The latter is characterised by breathlessness and abnormal sodium and water retention, resulting in oedema, with congestion of the lungs or peripheral circulation, or both (Dorland, 2009). As a result, typical treatments or "standard of care" (SOC) treatments of CHF patients comprise the administration of an angiotensin-converting enzyme (ACE) Inhibitor (eg enalapril and lisinopril) or an angiotensin receptor blocker (ARB) (eg valsartan, eprosartan and candesartan), in combination with diuretic therapy (usually the administration of a loop diuretic) to control the symptoms of CHF (Heart Foundation Guidelines, October 2011; and Aroll et al., 2010). For stable and chronic CHF patients, SOC treatments often comprise long term use of a diuretic agent such as furosemide. However, for the reasons given above, such long term use of a diuretic agent is undesirable.

The present applicant has realised that VSDL may be used as an adjuvant therapy to, for example, SOC treatments of CHF. As described herein, it has been found that VSDL is not only capable of achieving improvements in cardiac function (ie as shown by an increased cardiac index (CI), decreased or unchanged pulmonary capillary wedge pressure (PCWP) and decreased systolic and diastolic blood pressures), but can also achieve significant improvements in renal function and increased urine output. These changes are all desirable in the management of CHF including chronic CHF. However, the latter diuretic effects appear to be achieved in a "renal sparing" manner (ie the VSDL causes no functional decline in the kidney as evidenced by serum creatinine and glomerular filtration rate (GFR)) and this offers the additional benefit and possibility of, for example, wholly or partially avoiding long term use of a single diuretic agent (such as furosemide). In turn, this enables modified treatments intended to avoid or reduce the associated side-effects and/or concerns mentioned above, and/or enable improved treatment options for renally impaired CHF/ADCHF patients. Moreover, it is expected that VSDL will offer benefits in other contexts, in particular, other therapeutic treatments involving long term or extended use of a diuretic agent. In addition, it is considered that a similar benefit will be achieved by substituting or complementing the VSDL with another of the linear peptides derived from proANP (ie the peptide consisting of amino acids 1-30 of proANP (proANP 1-30/long-acting natriuretic peptide (LANP)), and the peptide consisting of amino acids 79-98 of proANP (proANP79-98/kaliuretic peptide)).

Thus, in a first aspect, the present invention provides a method for treating and/or preventing a disease or medical condition in a subject, comprising administering to the subject a diuretic agent in combination with a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof).

The method therefore utilises a proANP-derived linear peptide or a variant or modified peptide thereof. Those skilled in the art will understand that the term "linear peptide", as used herein, refers to the peptides cleaved from proANP that have a wholly linear sequence of amino acids with no cross-linking between non-adjacent amino acids (ie no disulphide bonds between non-adjacent cysteine residues) (cf the partially cyclic peptide ANP, which comprises a disulphide bond between Cys7 and Cys 23).

Preferably, the method of the first aspect comprises administering to the subject a diuretic agent in combination with vessel dilator (VSDL) or a variant or modified peptide thereof. It is considered that the VSDL (or variant or modified peptide thereof) acts as an adjuvant to the diuretic agent (ie such that it enhances or modifies the activity of the diuretic agent and/or therapeutic outcome achieved with the diuretic agent) or otherwise provides one or more other benefits (eg enabling lower dosages of the diuretic agent to be used and/or renal sparing to avoid toxicity or other damage to the kidney by the use of the diuretic agent).

The method of the first aspect may be used for treating and/or preventing any disease or medical condition typically treated by administering a diuretic agent or, in other words, any disease or medical condition where diuresis is desired. Examples of diseases and medical conditions that may be treated in accordance with the method of the invention include oedema associated with hypertension, cardio-renal syndrome (CRS) (eg Type I CRS; Ronco et al., 2010) and heart failure (HF), particularly congestive heart failure (both chronic CHF and ADCHF), pulmonary arterial hypertension (PAH), liver cirrhosis, ascites associated with liver cirrhosis, diabetes insipidus, glaucoma, septic shock, and renal diseases and conditions such as hypercalcemia, contrast-induced nephropathy (CIN), chronic kidney disease (CKD), acute renal failure (ARF)/acute kidney injury (AKI) (especially ARF caused by sepsis, where there is evidence that existing SOC/diuretic therapies provides little or no benefit; Sahu et al., 2011), chronic renal insufficiency (CRI) and/or nephrotic syndrome (where diuretic resistance is frequently observed; Wilcox, 2002).

The method of the first aspect may be particularly well suited to the treatment of subjects showing impaired kidney function (eg as determined by an eGFR of <75-90 ml/min/ 1.73 m$^2$ or acute diuretic resistance. In one embodiment, the method may be used for the treatment of subjects with impaired kidney function as determined by an eGFR in the range of 45-59 ml/min/1.73 m$^2$ or 30-44 ml/min/1.73 m$^2$. Also, in another embodiment, the method may be used for the treatment of subjects with impaired kidney function as determined by an eGFR in the range of 15-29 ml/min/1.73 m$^2$. It is also considered that the method of the fifth aspect may be particularly well suited to the treatment of subjects who develop refractory diuretic responsiveness (eg after prolonged use and/or elevated dosing of diuretic agents).

It is known in the art that some CHF/ADCHF patients on SOC diuretic treatment exhibit resistance and/or refractory diuretic responsiveness to the diuretic therapy. The phenomena of "diuretic resistance" (eg acute diuretic resistance) and refractory diuretic responsiveness is described in, for example, Ellison, 1999 and Valente, 2014.

The method of the first aspect may also be particularly well suited to subjects undergoing dialysis (which typically have an eGFR <15 ml/min/1.73 m$^2$).

The diuretic agent may be selected from osmotic diuretics (eg mannitol), high ceiling diuretics/loop diuretics (eg furosemide), thiazides (eg hydrochlorothiazide), carbonic anhydrase inhibitors (eg acetazolamide), and potassium-sparing diuretics (eg aldosterone antagonists such as spironolactone, and epithelial sodium channel blockers such as amiloride). However, preferably the diuretic agent is furosemide, spironolactone or a combination thereof.

The proANP-derived linear peptide (or variant or modified peptide thereof) may be administered before, after and/or simultaneously with the diuretic agent, and/or by the same or different mode of administration. For example, the diuretic agent may be administered by iv infusion and the proANP-derived linear peptide (or variant or modified peptide thereof) administered by sc infusion. Where the diuretic agent and proANP-derived linear peptide (or variant or modified peptide thereof) are administered separately, the period separating their administration may range from seconds (eg 30 seconds) to minutes (eg 30 minutes) or hours (eg 7 hours) to days (eg 1-5 days).

In one embodiment of the first aspect of the invention, the administration of the diuretic agent comprises standard of care (SOC) treatment for the disease or medical condition. That SOC treatment may further comprise administering one or more additional active agents.

The term "standard of care" treatment will be understood by those skilled in the art as referring to a treatment recognised or accredited (eg by a medical professional body and/or Governmental agency) as an appropriate treatment for a given disease or medical condition. There may be more than one SOC treatment for a given disease or medical condition. As mentioned above, for the treatment of CHF, an example of an SOC treatment comprises administering a vasodilator agent (eg an ACE inhibitor such as enalapril and lisinopril) in combination with a diuretic agent (usually furosemide (or another loop diuretic), or spironolactone or a combination thereof).

Thus, for the treatment of CHF, the method of the first aspect may comprise administering an ACE inhibitor with a diuretic agent and VSDL (or variant or modified peptide thereof) or another of the linear peptides derived from proANP, more preferably, an ACE inhibitor with furosemide and VSDL (or variant or modified peptide thereof). The ACE inhibitor will typically be administered simultaneously with the diuretic agent. The VSDL (or variant or modified peptide thereof) may be administered before, after and/or simultaneously with the ACE inhibitor and/or diuretic agent, and/or by the same or different mode of administration. Where the diuretic agent and VSDL (or variant or modified peptide thereof) are administered separately, the period separating their administration may range from seconds (eg 30 seconds) to minutes (eg 30 minutes) or hours (eg 7 hours) to days (eg 1-5 days). This enables the method to be conducted with a "staged" diuresis if desired; for example, a first stage of diuresis may be initially effected by the diuretic agent (eg by administration of furosemide) followed by a second stage of diuresis effected by VSDL (or variant or modified peptide thereof). A particular example of a method conducted in this manner may involve the oral administration of an amount of furosemide effective to achieve diuresis at a first required level for 1-2 hours, followed by iv or sc infusion of VSDL of an amount effective to achieve diuresis at a second required level (which may be the same as the first required level of different) for a period of 6-7 hours. Administration for staged diuresis may result in additive or synergistic diuretic effects leading to faster decongestion in severely ill subjects, especially those with hypernatremia. Moreover, this mode of treatment may mean decreased exposure to furosemide and its undesired side-effects. The VSDL would generally be infused so as to achieve a steady state plasma concentration (Css) as described in WO 2014/138796.

In the context of a long term or extended SOC treatment of a CHF patient, the method of the first aspect may be conducted over a period of, for example, 3 months to 20 years (in many cases, effectively the remainder of the subject's life). Over the course of the treatment period, the dosages of the diuretic agent and proANP-derived linear peptide (or variant or modified peptide thereof) may vary; preferably in a manner whereby the amount of the diuretic agent is reduced (possibly with a simultaneous increase in the dose of the proANP-derived linear peptide or variant or modified peptide thereof), including gradual dosage reduction until the diuretic agent is no longer being administered.

In another embodiment of the first aspect of the invention, the method may further comprise administering any vasodilator agent. The term "vasodilator agent" will be understood by those skilled in the art as referring to any agent that has a vasodilatory activity (ie causes dilatation of blood vessels to lower blood pressure) by acting, for example, directly on blood vessel walls to cause relaxation (eg hydrazinophthalazine drugs such as hydralazine (apresoline) which binds to and activates gated potassium channels in the endothelial cells of the blood vessel walls; calcium channel blockers such as nifedipine, verapamil and diltiazem; and non-linear (ie cyclic) natriuretic peptides (NPs) possessing vasodilatory activity such as ANP and brain natriuretic peptide (BNP) which bind to and activate natriuretic peptide receptor-A (NPRA) and/or natriuretic peptide receptor-B (NPRB) to cause the stimulation of intracellular guanylyl cyclase activity to convert GTP to cGMP which, in turn, stimulates cGMP-dependent protein kinase (PKG), which will then induce smooth muscle relaxation), and/or indirectly by, for example, modulating the renin-angiotensin-aldosterone system (RAAS) (eg ACE inhibitors and angiotensin receptor blockers (ARBs) such as valsartan, eprosartan and candesartan), causing an increase in the production of an endogenous vasodilator such as nitric oxide (NO), and/or through inhibition of endogenous vasoconstrictors such as endothelin. Relaxin (including human relaxin-2 such as serelaxin (RLX030), Novartis AG, Basel, Switzerland) is an example of a vasodilator agent that causes dilatation of blood vessels by a number of different mechanisms, including increasing NO production (Bathgate et al. 2013), inhibiting vasoconstrictors (Teichman et al., 2009) and, also, by binding to and activating the endothelial B2 receptor of endothelial cells in the blood vessel walls (Teichman et al., 2010). Other examples of suitable vasodilator agents include nitroxy (HNO) donor compounds (eg CXL-1427; Cardioxyl Pharmaceuticals, Inc., Chapel Hill, N.C., United States of America) and β-arrestin-biased ligands (eg TRV027; Trevena Inc., King of Prussia, Pa., United States of America). In one preferred form of this embodiment, the method comprises administering to the subject a diuretic agent in combination with VSDL and relaxin (eg serelaxin) or a variant or modified peptide thereof. In another preferred form of this embodiment, the method comprises administering to the subject a diuretic agent in combination with VSDL and BNP. As used herein, the term "vasodilator agent" does not include VSDL (or variants or modified peptides thereof).

The method of the first aspect employs a proANP-derived linear peptide (or variant or modified peptide thereof). As used herein, a "variant" of a proANP-derived linear peptide may be a natural variant (such as a natural variant including one or more amino acid substitution, addition or deletion). Otherwise, a variant may be a modified peptide such as a modified VSDL peptide. Modified proANP-derived linear peptides include not only variant peptides (ie non-natural variants variant including one or more amino acid substitution, addition or deletion), but also derivatives and mimetics of a native peptide (eg VSDL) which include minor variations in the amino acid sequence that do not result in any substantial decrease or variation in biological activity (eg shows no more than a 10% decrease or variation in biological activity of the peptide from which it is derived, as measured by the ill vitro vasodilation assay (using aortic strips) described by DL Vesely in U.S. Pat. No. 5,691,310 or assay for increased cyclic GMP levels described by DL Vesely (Vesely et al. 1987). These variations may include conservative amino acid substitutions. Some specific examples of suitable amino acid substitutions within the VSDL peptide may include Pro-Gln (especially at position 10 of the VSDL peptide), Thr→Ala (especially at position 28 of the VSDL peptide), Glu→Asp (especially at position 30 of the VSDL peptide), and Ser→Asn (especially at position 32 of the VSDL peptide). Suitable mimetics of proANP-derived linear peptides may be designed using any of the methods well known to those skilled in the art for designing mimetics of peptides based upon amino acid sequences in the absence of secondary and tertiary structural information (Kirshenbaum et al., 1999). For example, peptide mimetic compounds may be produced by modifying amino acid side chains to increase the hydrophobicity of defined regions of the peptide (eg substituting hydrogens with methyl groups on aromatic residues of the peptides), substituting amino acid side chains with non-amino acid side chains (eg substituting aromatic residues of the peptides with other aryl groups), and substituting amino- and/or carboxy-termini with various substituents (eg substituting aliphatic groups to increase hydrophobicity). Alternatively, mimetic compounds of a proANP-derived linear peptide may be a so-called peptoid (ie non-peptide) which includes modification of the peptide backbone (ie introducing amide bond surrogates by, for example, replacing the nitrogen atoms in the backbone with carbon atoms), or includes N-substituted glycine residues, one or more D-amino acids (in place of L-amino acid(s)) and/or one or more α-amino acids (in place of β-amino acids or γ-amino acids). Further, suitable mimetic compounds of a proANP-derived linear peptide include "retro-inverso peptides" where the peptide bonds are reversed and D-amino acids assembled in reverse order to the order of the L-amino acids in the peptide sequence upon which the mimetic is based, and other non-peptide frameworks such as steroids, saccharides, benzazepine 1,3,4-trisubstituted pyrrolidinone, pyridones and pyridopyrazines.

More preferably, the method employs VSDL with a native sequence, such as the native amino acid sequence of human VSDL (derived from residues 31-67 of human proANP). The native amino acid sequence of human VSDL is provided in WO 2012/019237 (the content of which is hereby incorporated by reference in its entirety).

Other suitable native VSDL peptides may include those of *Pongo pygmaeus* (common orangutan), *Macaca mulatta* (rhesus monkey) and *Felis catus*. The amino acid sequences of these VSDL peptides are provided in WO 2012/019237 (the content of which is hereby incorporated by reference in its entirety).

The proANP-derived linear peptide (or variant or modified peptide thereof) may be produced by any of the standard protein synthesis methods well known to those skilled in the art or, more preferably, by recombinant techniques involving, for example, the introduction of a polynucleotide molecule encoding the particular peptide into a suitable host cell (eg a host cell selected from bacterial cells such as *E. coli, Streptomyces* and *S. typhimurim*; fungal cells such as yeast cells; insect cells such as *Drosophila* S2 and *Spodoptera* Sf9 cells; animal cells such as Chinese hamster ovary (CHO), monkey kidney (COS) cells and human embryonic kidney 293 (HEK 293) cells; and plant cells) and culturing the cell under conditions suitable for the expression of the particular peptide.

Preferably, the proANP-derived linear peptide (or variant or modified peptide thereof) will be administered as a composition consisting of a simple solution or suspension of the peptide in a pharmaceutically-acceptable carrier. However, it will be readily appreciated by those skilled in the art, that the proANP-derived linear peptide (or variant or modified peptide thereof) may be bound or associated with a carrier molecule (eg a carrier protein or fusion partner such as human serum albumin (HSA) or a polysaccharide (eg Dextran) or polyether (eg polyethylene glycol)) in order to modulate the biological activity and/or serum half-life time of the proANP-derived linear peptide (or variant or modified peptide thereof).

The term "pharmaceutically-acceptable carrier" as used herein refers to any pharmaceutically- or veterinary-acceptable solvent, suspending agent or vehicle for delivering the proANP-derived linear peptide (or variant or modified peptide thereof) to the subject. The carrier may include one or more pharmaceutical additives of a type appropriate to, for example, infusion (eg excipients, preservatives, stabilisers etc).

The administration of the proANP-derived linear peptide (or variant or modified peptide thereof) by infusion is, preferably, achieved intravenously (iv) (which is particularly suitable in the hospital setting) or subcutaneously (sc) (which is suitable for both hospitalised patient and out-of-hospital administration) as a bolus and/or sustained infusion (eg for a period of 30 minutes, 1 hour or longer). For example, infusion may be via a standard catheter or implantable drug port (eg a Port-a-Cath®; Smiths Medical MD, Inc., St. Paul Minn., United States of America), or otherwise achieved using a drug infusion pump (eg implantable drug infusion pumps such as an Alzetc® osmotic pump (Durect Corporation, Cupertino Calif., United States of America) and a Duros® device (Intarcia Therapeutics, Inc., Hayward Calif., United States of America), or a drug infusion pump for subcutaneous (sc) administration such as a Paradigm™ device (Medtronic Australasia Pty Ltd, Gladesville NSW, Australia) all of which can provide a controlled release of the proANP-derived linear peptide (or variant or modified peptide thereof). The use of an implantable drug port or drug infusion pump is particularly well suited for long term or extended treatments according to the method of the first aspect. Typically, the proANP-derived linear peptide (or variant or modified peptide thereof) will be infused at a constant rate, however, in some cases it may be desirable to employ a drug infusion pump employing a feedback control mechanism (eg a feedback linked to measurement of oedema (in the lung) or other surrogate marker) to control release of the proANP-derived linear peptide (or variant or modified peptide thereof).

It will be appreciated by those skilled in the art that numerous variations and/or routine modifications may be made to the method of the first aspect without departing from the spirit or scope of the invention as broadly described. For example, it will be understood that the amount and frequency of administration of the proANP-derived linear peptide (or variant or modified peptide thereof) for any particular subject may be varied and will depend upon a variety of factors including the activity of the particular proANP-derived linear peptide (or variant or modified peptide thereof) that is utilised, the metabolic stability and length of action of the particular proANP-derived linear peptide (or variant or modified peptide thereof), the age, body weight, general health, sex and diet of the particular subject, and the time of administration, rate of excretion, drug combination and severity of the disease or medical condition being treated.

Generally, where the proANP-derived linear peptide (or variant or modified peptide thereof) is administered intravenously (iv), it will be administered in an amount in the range of about 0.1 to 75 µg/kg/day, but more preferably in the range of about 0.1 to 25 µg/kg/day, and still more preferably in the range of about 0.1 to 20 µg/kg/day. However, where administered subcutaneously (sc), the proANP-derived linear peptide (or variant or modified peptide thereof) will generally be administered in an amount in the range of about 10 to 2000 µg/kg/day, but more preferably in the range of about 250 to 1750 µg/kg/day, and still more preferably in the range of about 500 to 1500 µg/kg/day.

As mentioned above, in an embodiment of the first aspect of the invention, the method may further comprise administering to the subject a natriuretic peptide (NP) possessing vasodilatory activity. Suitable NPs that may be employed in this embodiment include active peptide fragments of the atrial natriuretic peptide (ANP) prohonnone such as any peptide fragment from within the C-terminal amino acids 94-126 that is active inasmuch as the peptide fragment has guanylate cyclase (GC) agonist activity (ie. capable of stimulating a GC enzyme) including ANP (amino acids 99-126) and variants or modified peptides thereof) and urodilatin (amino acids 95-126) and variants and modified peptides thereof, BNP (and variants and modified peptides thereof) and chimaeric forms of such natriuretic peptides such as CDNP (Dickey et al., 2008) possessing vasodilatory activity. BNP is a 32 amino acid peptide produced in the ventricular myocardium. The amino acid sequence of human BNP is provided in Kambayashi et al., 1990 (the content of which is hereby incorporated by reference in its entirety). The BNP peptide includes a cross-linking disulphide bond between the two Cys residues at positions 10 and 26 to form a cyclic structure comprising 17 amino acids. A recombinant form of human BNP, known as nesiritide, has been approved by the FDA for the treatment of ADCHF. However, subsequent studies have shown that it is not associated with a change in patient mortality or re-hospitalisation rate (O'Conner et al., 2011). Moreover, it has been found that nesiritide does not increase diuresis in ADCHF patients (Gottlieb, 2013). While not wishing to be bound by theory, the present applicant considers that the activity of BNP may be inhibited by high chloride ion ($Cl^-$) concentration in the tubule lumen caused by the inhibition of $Cl^-$ ion reabsorption by a loop diuretic such as furosemide. It is considered that co-administration of a proANP-derived linear peptide (or variant or modified peptide thereof) such as VSDL overcomes this inhibition since its function is not limited by ion concentrations such as $Cl^-$ mentioned above. Thus, in one particular form of the embodiment of the first aspect of the invention wherein the subject is also administered with a natriuretic peptide (NP), the method comprises administering the subject with an ACE inhibitor in combination with a diuretic agent (preferably a loop diuretic such as furosemide), a proANP-derived linear peptide (or a variant or modified peptide thereof), especially VSDL or a variant or modified peptide thereof, and BNP (or a variant or modified peptide thereof). The BNP (or a variant or modified peptide thereof) may be administered in a relatively low dosage such as, for example, 3 to 15 µg/kg/day, while the proANP-derived linear peptide (or a variant or modified peptide thereof) may be administered in a relatively high dose such as, for example, 20 to 75 µg/kg/day.

Further, in some embodiments of the first aspect of the invention, the method may further comprise administering to the subject an adenosine A1 receptor antagonist such as, for example, rolofylline, theophylline and caffeine.

In a second aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) in the preparation of a medicament for treating and/or preventing a disease or medical condition in a subject, wherein the peptide (or variant or modified peptide thereof) is administered in combination with a diuretic agent.

In a third aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) for treating and/or preventing a disease or medical condition in a subject, wherein the peptide (or a variant or modified peptide thereof) is administered in combination with a diuretic agent.

In a fourth aspect, the present invention provides a kit comprising a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) and a diuretic agent optionally with instructions for the use of said kit in a method for treating and/or preventing a disease or medical condition in a subject.

The uses and kit of the second to fourth aspects are particularly suitable for a disease or medical condition where diuresis is desired, such as oedema associated with hypertension, cardio-renal syndrome (CRS) (eg Type I CRS) and heart failure (HF), particularly congestive heart failure (both chronic CHF and ADCHF), pulmonary arterial hypertension (PAH), liver cirrhosis, ascites associated with liver cirrhosis, diabetes insipidus, glaucoma, septic shock and renal diseases and conditions such as hypercalcemia, contrast-induced nephropathy (CIN), chronic kidney disease (CKD) and acute renal failure (ARF)/acute kidney injury (AKI), chronic renal insufficiency (CRI) and/or nephrotic syndrome; and especially where the subject shows impaired kidney function (eg as determined by an eGFR of <75-90 ml/min/1.73 m$^2$ or acute diuretic resistance. In one embodiment, the uses and kit may be used for the treatment of subjects with impaired kidney function as determined by an eGFR in the range of 45-59 ml/min/1.73 m$^2$ or 30-44 ml/min/1.73 m$^2$. Also, in another embodiment, the uses and kit may be used for the treatment of subjects with impaired kidney function as determined by an eGFR in the range of 15-29 ml/min/1.73 m$^2$. It is also considered that the uses and kits may be particularly suited to the treatment of subjects showing refractory diuretic responsiveness. Further, it is considered that the uses and kits may also be particularly well suited to the treatment of subjects undergoing dialysis.

The uses and kit of the second to fourth aspects utilises a proANP-derived linear peptide or a variant or modified peptide thereof. Preferably, the proANP-derived linear peptide (or a variant or modified peptide thereof) is vessel dilator (VSDL) or a variant or modified peptide thereof.

The diuretic agent may be selected from osmotic diuretics (eg mannitol), high ceiling diuretics/loop diuretics (eg furosemide), thiazides (eg hydrochlorothiazide), carbonic anhydrase inhibitors (eg acetazolamide), and potassium-sparing diuretics (eg aldosterone antagonists such as spironolactone, and epithelial sodium channel blockers such as amiloride). However, preferably the diuretic agent is furosemide.

The uses may be made with standard of care (SOC) treatment for the disease or medical condition. As such, for treatment of CHF, the proANP-derived linear peptide (or a variant or modified peptide thereof) and diuretic agent may be administered in further combination with an ACE inhibitor.

In a fifth aspect, the present invention provides a method for treating and/or preventing a disease or medical condition in a subject, comprising administering to the subject a vasodilator agent in combination with a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof).

The method of the fifth aspect utilises a proANP-derived linear peptide or a variant or modified peptide thereof. Preferably, the proANP-derived linear peptide (or a variant or modified peptide thereof) is vessel dilator (VSDL) or a variant or modified peptide thereof. It is considered that the proANP-derived linear peptide (or variant or modified peptide thereof) acts as an adjuvant to the vasodilator agent (ie such that it enhances the activity of the vasodilator agent) or otherwise provides one or more other benefits (eg the proANP-derived linear peptide provides diuretic activity while the vasodilator agent provides vasodilatory activity).

The method of the fifth aspect may be used for treating and/or preventing any disease or medical condition typically treated by administering an agent or agents for lowering blood pressure and causing diuresis. Examples of diseases and medical conditions that may be treated in accordance with the method of the invention include oedema associated with hypertension, cardio-renal syndrome (CRS) (eg Type I CRS; Ronco et al., 2010) and heart failure (HF), particularly congestive heart failure (both chronic CHF and ADCHF), pulmonary arterial hypertension (PAH), liver cirrhosis, ascites associated with liver cirrhosis, diabetes insipidus, glaucoma, septic shock, and renal diseases and conditions such as hypercalcemia, contrast-induced nephropathy (CIN), chronic kidney disease (CKD) and acute renal failure (ARF)/acute kidney injury (AKI), chronic renal insufficiency (CRI) and/or nephrotic syndrome.

The method of the fifth aspect may be particularly well suited to the treatment of subjects showing impaired kidney function (eg as determined by an eGFR of <75-90 ml/min/1.73 m$^2$) or acute diuretic resistance. In one embodiment, the method may be used for the treatment of subjects with impaired kidney function as determined by an eGFR in the range of 45-59 ml/min/1.73 m$^2$ or 30-44 ml/min/1.73 m$^2$. Also, in another embodiment, the method may be used for the treatment of subjects with impaired kidney function as determined by an eGFR in the range of 15-29 ml/min/1.73 m$^2$. It is also considered that the method of the fifth aspect may be particularly suited to the treatment of subjects showing refractory diuretic responsiveness. Further, it is considered that the method of the fifth aspect may also be particularly well suited to the treatment of subjects undergoing dialysis.

The vasodilator agent may be any agent that has a vasodilatory activity by acting directly on blood vessel walls to cause relaxation (eg hydrazinophthalazine drugs such as hydralazine (apresoline); calcium channel blockers such as nifedipine, verapamil and diltiazem; and natriuretic peptides (NPs) possessing vasodilatory activity such as ANP, BNP, urodilatin and chimaeric CDNP) and/or indirectly by, for example, modulating the renin-angiotensin-aldosterone system (RAAS) (eg ACE inhibitors and angiotensin receptor blockers (ARBs) such as valsartan and candesartan), causing an increase in the production of an endogenous vasodilator such as nitric oxide (NO), and/or through inhibition of endogenous vasoconstrictors such as endothelin.

In one embodiment of the fifth aspect of the invention, the method comprises administering to the subject a proANP-derived linear peptide (or a variant or modified peptide thereof) and relaxin (eg serelaxin) or a variant or modified peptide thereof.

In another embodiment of the fifth aspect of the invention, the method comprises administering to the subject a proANP-derived linear peptide (or a variant or modified peptide thereof) and BNP (or a variant or modified peptide thereof).

In yet another embodiment of the fifth aspect of the invention, the method comprises administering to the subject a proANP-derived linear peptide (or a variant or modified peptide thereof) and an ARB. Preferably, the ARB is valsartan. The valsartan may be provided in combination with an inhibitor of neprilysin (also known as neutral endopeptidase; NEP) such as a NEP inhibitor selected from the group consisting of AHU-377 (sacubitril), (4S,7S,10aS)-5-oxo-4-{[(2S)-3-phenyl-2-sulfanylpropanoyl]amino}-2,3,4,7,8,9,10,10a-octahydropyrido[6,1-b][1,3]thiazepine-7-carboxylic acid (omapatrilat; which inhibits both NEP and ACE), benzyl N-(3-{[(2S)-2-amino-4-(methylthio)butyl]dithio}-2-benzylpropanoyl)-L-phenylalaninate (RB-101), and (R)-2-({1-[(5-ethyl-1,3,4-thiadiazol-2-yl)carbamoyl]cyclopentyl}methyl)valeric acid (UK-414,495). In one particular example, the ARB may comprise a single molecule comprising a valsartan moiety and an AHU-377 moiety, as has been described by Ruilope et al., 2010 (designated LCZ696; Novartis).

In yet still another embodiment of the fifth aspect of the invention, the method comprises administering to the subject a vasodilator agent in combination with a proANP-derived linear peptide (or a variant or modified peptide thereof) and a neprilysin inhibitor (eg AHU-377). Neprilysin is a zinc-dependent metalloprotease that cleaves peptides at the amino side of hydrophobic residues and is known to inactivate several peptide hormones including bradykinin, ANP and BNP (Schubert-Zsilavecz, 2010/2011). While not wishing to be bound by theory, it is also considered that neprilysin catalyses the breakdown of the proANP-derived linear peptides such as VSDL and therefore, the combination of a vasodilator agent, proANP-derived linear peptide (or a variant or modified peptide thereof), preferably VSDL, and a neprilysin inhibitor offers the potential of greatly enhanced vasodilatory activity and diuresis by virtue of achieving increased circulating levels of proANP-derived linear peptide (eg increased circulating levels of VSDL comprising both endogenous VSDL and administered, exogenous VSDL) to enhance diuresis, and increased circulating levels of endogenous ANP and BNP (both contributing vasodilatory activity along with that of the vasodilator agent).

In the method of the fifth aspect, the administration of the proANP-derived linear peptide (or variant or modified peptide thereof) is preferably by infusion achieved, for example, intravenously (iv) or subcutaneously (sc). The infusion may be via a standard catheter or implantable drug port, or otherwise achieved using a drug infusion pump or a drug infusion pump for subcutaneous (sc) administration, all of which can provide a controlled release of the proANP-derived linear peptide (or variant or modified peptide thereof). The use of an implantable drug port or drug infusion pump is particularly well suited for long term or extended treatments according to the method of the fifth aspect. Typically, the proANP-derived linear peptide (or variant or modified peptide thereof) will be infused at a constant rate, however, in some cases it may be desirable to employ a drug infusion pump employing a feedback control mechanism (eg a feedback linked to measurement of oedema (in the lung) or other surrogate marker) to control release of the proANP-derived linear peptide (or variant or modified peptide thereof).

In a sixth aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) in the preparation of a medicament for treating and/or preventing a disease or medical condition in a subject, wherein the peptide (or variant or modified peptide thereof) is administered in combination with a vasodilator agent.

In a seventh aspect, the present invention provides the use of a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) for treating and/or preventing a disease or medical condition in a subject, wherein the peptide (or a variant or modified peptide thereof) is administered in combination with a vasodilator agent.

In an eighth aspect, the present invention provides a kit comprising a peptide selected from the group consisting of vessel dilator (VSDL) or a variant or modified peptide thereof, long-acting natriuretic peptide (LANP) or a variant or modified peptide thereof, and kaliuretic peptide (KP) or a variant or modified peptide thereof, or a combination of said peptides (or variants or modified peptides thereof) and a vasodilator agent optionally with instructions for the use of said kit in a method for treating and/or preventing a disease or medical condition in a subject.

The uses and kit of the sixth to eighth aspects are particularly suitable for a disease or medical condition where diuresis is desired, such as oedema associated with hypertension, cardio-renal syndrome (CRS) (eg Type I CRS) and heart failure (HF), particularly congestive heart failure (both chronic CHF and ADCHF), pulmonary arterial hypertension (PAH), liver cirrhosis, ascites associated with liver cirrhosis, diabetes insipidus, glaucoma, septic shock and renal diseases and conditions such as hypercalcemia, contrast-induced nephropathy (CIN), chronic kidney disease (CKD) and acute renal failure (ARF)/acute kidney injury (AKI), chronic renal insufficiency (CRI) and/or nephrotic syndrome; and especially where the subject shows impaired kidney function (eg as determined by a creatinine clearance of <20 ml/min). In one embodiment, the uses and kit are particularly suitable for use with subjects with impaired kidney function as determined by an eGFR of <75-90 ml/min/1.73 $m^2$) or acute diuretic resistance. In one embodiment, the uses and kit may be used for the treatment of subjects with impaired kidney function as determined by an eGFR in the range of 45-59 ml/min/1.73 $m^2$ or 30-44 ml/min/1.73 $m^2$. Also, in another embodiment, the uses and kit may be used for the treatment of subjects with impaired kidney function as determined by an eGFR in the range of 15-29 ml/min/1.73 $m^2$. It is also considered that the uses and kit may be particularly suited to the treatment of subjects showing refractory diuretic responsiveness. Further, it is considered that the uses and kits of the sixth to eighth aspects may also be particularly well suited to the treatment of subjects undergoing dialysis.

The uses and kit of the sixth to eighth aspects utilise a proANP-derived linear peptide or a variant or modified peptide thereof. Preferably, the proANP-derived linear peptide (or a variant or modified peptide thereof) is vessel dilator (VSDL) or a variant or modified peptide thereof.

The vasodilator agent may be any agent that has a vasodilatory activity by acting directly on blood vessel walls to cause relaxation (eg hydrazinophthalazine drugs such as hydralazine (apresoline); calcium channel blockers such as nifedipine, verapamil and diltiazem; and natriuretic peptides (NPs) possessing vasodilatory activity such as ANP, BNP, urodilatin and chimaeric CDNP) and/or indirectly by, for example, modulating the renin-angiotensin-aldosterone system (RAAS) (eg ACE inhibitors), causing an increase in the production of an endogenous vasodilator such as nitric oxide (NO), and/or through inhibition of endogenous vasoconstrictors such as endothelin.

In a ninth aspect, the present invention provides a kit comprising VSDL (or a variant or modified peptide thereof) and a natriuretic peptide such as any active peptide fragment from within the C-terminal amino acids 94-126 of atrial natriureic peptide prohormone (proANP) such as ANP (or a variant or modified peptide thereof) and urodilatin (or a variant or modified peptide thereof), BNP (or a variant or modified peptide thereof) or a chimaeric form of such natriuretic peptides, optionally with instructions for the use of said kit in a method for treating CHF or ADCHF.

The kit of the ninth aspect may be particularly suitable for use with standard of care (SOC) treatment for CHF or ADCHF.

In a tenth aspect, the present invention provides a kit comprising VSDL (or a variant or modified peptide thereof) and a vasodilator agent such as relaxin optionally with instructions for the use of said kit in a method for treating CHF or ADCHF.

In an eleventh aspect, the present invention provides a kit comprising vessel dilator (VSDL) (or a variant or modified peptide thereof), a vasodilator agent such as relaxin and a neprilysin inhibitor such as sacubitril (AHU-377), optionally with instructions for the use of said kit in a method for treating CHF or ADCHF.

The invention is hereinafter described by way of the following, non-limiting example and accompanying figures.

EXAMPLE

Example 1 Adjuvant VSDL Therapy of Stable Congestive Heart Failure (CHF) Patients Materials and Methods
Formulation VSDL in the form of a white lyophilised powder (synthesised using standard protein synthesis method by Auspep Pty Ltd, Parkville, VIC, Australia), stored in an ultra-low freezer (−80° C.), was reconstituted in a vial with 10 ml of 0.9% saline (preservative free) and aseptically transferred into a 20 ml syringe (that connects to a cannula) before use.

Participants

A first study was conducted with a cohort of eight (8) test adult patients, both male and female, with a history of stable, chronic congestive heart failure and moderate renal impairment that had been selected on the basis of the following Inclusion and Exclusion criteria:

Inclusion Criteria:

1) a left ventricular ejection fraction (LVEF) of ≤45% measured by Trans-Thoracic electrocardiogram (TTE) or nuclear imaging (measurement within 90 days prior to screening), 2) a glomerular filtration rate (GFR) ≥25 ml/min/1.73 m$^2$ and <70 ml/min/1.73 m$^2$ (Cockroft Gault calculation), and 3) were non-pregnant females as evidenced by serum pregnancy test at screening and negative urine pregnancy test pre-dose at Day 1 (for women of child bearing potential only) or were of non-child bearing potential (as defined as having amenorrhea for at least 2 years prior to study entry or who have been surgically sterilised).

Exclusion Criteria:

1) evidence in the emergency department (ED) of myocardial infarction (MI) or high risk acute coronary syndrome within past 6 weeks, as determined by creatinine kinase (CK)/creatinine kinase muscle-brain isoenzyme (CK-MB) ≥2 times upper limit of normal or elevation of troponin T at baseline >0.1 or as determined by TTE, 2) sustained hypotension (SBP<90 mmHg) and/or cardiogenic shock and/or volume depletion, 3) persistent, uncontrolled hypertension (SBP>180 mmHg), 4) congenital heart defects (includes ventricular septal defect, atrial septal defect, patent ductus arteriosus, tetralogy of fallot, tricuspid atresia), 5) cardiac surgery within past 4 weeks, 6) diastolic heart failure (preserved left ventricular function—as determined by echocardiogram (ECG) <24 hrs pre-patient enrolment), 7) severe valvular heart disease: aortic stenosis <1.0 cm2, any idiopathic hypertrophic subaortic stenosis or hypertrophic obstructive cardiomyopathy, aortic regurgitation grade 4 and mitral regurgitation grade 4, as determined by ECG <24 hrs pre-patient enrolment, 8) history of cerebrovascular accident (within past 4 weeks) as determined by MRI or Computerised Tomography (CT) scan, 9) acute or chronic active infection, including pneumonia and urinary tract infection documented by appropriate culture result, 10) significant renal impairment as determined by a creatinine clearance of <60 ml/min, and 11) prior participation in any other clinical trial within past 30 days.

Treatment

All patients underwent existing standard of care (SOC) treatment for the condition for which they presented. These treatments were diuretic therapy (ie administration with furosemide or spironolactone) and an antihypertensive drug(s) (eg an Angiotensin Converting Enzyme (ACE) inhibitor, beta blocker agent and calcium channel blocker agent). In addition, the patients also received an adjuvant VSDL treatment as follows: A single dose of 250 mg of VSDL on Day 1 and 500 mg of VSDL on Day 2, by subcutaneous (sc) bolus.

Results

Pharmacokinetics

Results of the study described in this example indicate that the bioavailability of VSDL, when administered as a single sc bolus, is 19.2% with a population variability of 28%. The absorption and elimination pharmacokinetics are detailed in Table 1.

Vasodilation

There was a significant drop in systolic and diastolic blood pressures in the stable CHF patients treated with VSDL (Table 2). However, none of these resulted in symptomatic hypotension.

TABLE 1

Pharmacokinetics of sc VSDL

| Parameter | Description | Pop value | Unit | se (%) | BSV | Unit | se (%) |
|---|---|---|---|---|---|---|---|
| CL | Maximum Elimination rate | 26.8 | L/h | 15.3 | 56.70 | % | 52.20 |
| V | Central volume | 13.20 | L | 20.40 | 56.70 | % | 52.20 |
| V2 | S.C. bolus V scaling factor | 1.62 | ratio | 49.1 | | | |
| V3 | S.C. infusion V scaling factor | 3.65 | ratio | 11.5 | | | |
| KA | Absorption rate constant | 0.625 | 1/h | 17.90 | 38.60 | % | 164.40 |
| LGT | Logit F value | −1.00 | — | 281.00 | 1.46 | — | 54.20 |
| F | Bioavailability | 26.894 | % | — | — | — | — |
| FVOL | Infused volume on F | 1.590 | ratio | 24.8 | | | |
| ETASHARE | Random effect scalinmg factor | 1.000 | ratio | 8.8 | — | — | — |
| RUVCVIV | Residual Error (Proportional, I.V.) | 0.336 | ratio | 22.00 | — | — | — |
| RUVADDIV | Residual Error (Additive, I.V.) | 0.248 | ng/ml | 28.70 | — | — | — |
| RUVCVSC | Residual Error (Proportional, S.C.) | 0.259 | Ratio | 18.20 | — | — | — |
| RUVADDSC | Residual Error (Additive, S.C.) | 0.070 | ng/ml | 95.60 | — | — | — |

Pop value = Typical value in population,
BSV = Between subject variability,
RUV = Residual unexplained variability,
se = standard error or parameter estimate (uncertainty) se determined via Importance Sampling

TABLE 2

Blood pressures in patients treated with VSDL ($p < 0.05$)

| | Baseline | 10 ng/kg | 20 ng/kg |
|---|---|---|---|
| Systolic blood pressure (mmHg) | 119 ± 15 | 122 ± 10 | 115 ± 19 |
| Diastolic blood pressure (mmHg) | 65 ± 10 | 64 ± 7 | 65 ± 6 |

Discussion

Adjuvant treatment with VSDL helps unload the congested CHF patient via stabilised and improved renal function resulting in improved cardiac function.

Example 2 Adjuvant VSDL Therapy of Patients Showing Acute Exacerbations of Chronic Congestive Heart Failure (CHF) or Acute Decompensated Congestive Heart Failure (ADCHF/ADHF) Patients A second study was conducted with a population of eighteen (18) test adult CHF patients, both male and female, in order to further evaluate the improvement in renal and cardiac function in stable CHF patients given VSDL (by sc administration) in addition to standard of care (SOC) treatment.

Materials and Methods

Participants

Participants were selected on the basis of the Inclusion and Exclusion criteria given in Example 1. Key requirements were that the patients were aged 18 years or older and had a history of stable, symptomatic CHF, with a LVEF of ≤45% measured by TTE or gated blood pool scan, performed within 90 days prior to screening. In addition, selected patients were required to have a plasma brain natriuretic peptide (BNP) concentration of ≥100 pg/mL and a GFR ≥25 mL/min and <70 mL/min as calculated by the Cockroft Gault calculation (ie moderate renal impairment). On the other hand, the presence of acute MI (ie as indicated by ST elevation and/or elevation of Troponin-T) or evidence of MI or other high risk acute coronary syndrome within the past 6 weeks, hypotension (ie systolic blood pressure (SBP) <90 mmHg), persistent and/or uncontrolled hypertension (SBP>180 mmHg), cardiogenic shock or any other clinical condition that would contraindicate administration of an agent with potent vasodilatory effects, excluded patients from participating in the study. Participants in this study also had standard exclusion criteria that accompany pulmonary artery (SG) catheterisation.

Study Design

The study was an open-label, sequential group, continuous sc infusion study conducted at a single centre. Two steady-state concentration levels (Css) of VSDL were targeted, approximately 10 ng/mL (n=2 lead-in, and n=10, cohort 1) and 20 ng/mL (n=6, cohort 2). The two lead-in patients were treated with similar dose regimens to confirm that the measured plasma concentrations were in agreement with the targeted Css. Two patients from cohort 1 and all 6 patients from cohort 2 underwent pulmonary artery Swan-Ganz (SG) catheterisation to enable haemodynamic monitoring.

Dosing Regimens

VSDL prepared as described in Example 1, was administered via sc 6 or 12 hour infusion into the lower abdomen at a maximum volume rate of 350 µL/hr (ie approximately 6 µL/min). The rate of infusion of VSDL for the targeted Css level of 10 ng/mL was either 900 µg/hr (0.3 mL/hr) for 12 hrs or a bimodal infusion of 900 µg/hr for 5 hrs followed by 550 µg/hr (0.18 mL/hr) for 7 hrs. The rate of infusion of VSDL for the targeted Css level of 20 ng/mL was bimodal; 1800 µg/hr (0.20 mL/hr) for 5 hrs followed by 1100 µg/hr (0.12 mL/hr) for 7 hrs (see WO 2014/138796). For the lead-in patients, the infusions were performed at 900 µg/hr for 6 hrs.

Statistical Analysis

R Studio (version 4) and GraphPad Prism (GraphPad Software, version 6) were used for all statistical analyses. Statistically significant changes from base line for all parameters were tested using with linear mixed effects model or one-way repeated measures ANOVA with Bonferroni correction. A p value of 0.05 was set for statistically significant differences. All data are reported as mean±s.d or mean (95% CI).

Results

Patients were assigned to the lead-in (n=2), 10 ng/ml (n=10) and 20 ng/ml (n=6) infusion groups respectively. Baseline characteristics for all patients in the study are shown in Table 3.

VSDL and Cardiac Parameters Including Blood Pressure

Regression of cardiac output on time accommodating repeated measures demonstrated that patients treated with VSDL had a significant increase in cardiac output equating to an increase on average of 0.000472 L/min above baseline (t=3.16; p≤0.05) (FIG. 1). Additionally, there were no severe adverse events reported and all reported adverse events were self-limiting, recovering without need for intervention.

Analysis of mean blood pressures based on post infusion time demonstrated that there were no significant drops in blood pressures from baseline in patients treated with VSDL, (p=0.4) (Table 4). During the 24 hour time period, the average drop in blood pressure in the 10 ng/ml cohort was −8/−5 mmHg (systolic/diastolic) and in the 20 ng/ml cohort, the average drop in blood pressure was −13/−8 mmHg. Throughout the 12 hour infusion period, the mean drop was −8/−6 mmHg and −14/−7 mmHg in the two cohorts respectively. There was no significant drop in blood pressures even in patients with baseline blood pressures ≤105/60 mmHg; with the average blood pressure drop in this group during the infusion being −4/−3 mmHg.

TABLE 3

Patient characteristics

| Parameter | Mean | Min-Max |
|---|---|---|
| Age (years) | 78 ± 10 | (53-95) |
| Male gender n (%) | 15 | (83) |
| Body-mass Index (kg/m$^2$) | 30 ± 5 | (25-44) |
| Heart Rate (beats/min) | 63 ± 7 | (50-76) |
| Systolic Blood Pressure (mmHg) | 118 ± 14 | (88-151) |
| Diastolic Blood Pressure (mmHg) | 65 ± 10 | (50-92) |
| Pulmonary Capillary Wedge Pressure (mmHg) | 10 ± 4 | (5-18) |
| Cardiac Output (L/min) | 4 ± 1 | (3-6) |
| Ejection Fraction (%) | 35 ± 8 | (17-45) |
| Urine Sodium (mmol/L) | 82 ± 25 | (39-144) |
| Plasma Sodium (mmol/L) | 139 ± 3 | (133-145) |
| eGFR (mL/min/1.73 m$^2$) | 37 ± 11 | (19-54) |
| Patients on Diuretics | 16 (89%) | |
| Furosemide | 15 (83%) | |
| Spironolactone | 12 (67%) | |
| Both | 11 (61%) | |

TABLE 4

Blood pressures based post infusion times

| | Systolic Blood Pressure (mmHg) | | | | Diastolic Blood Pressure (mmHg) | | | |
|---|---|---|---|---|---|---|---|---|
| Time Points | Baseline | 0.5-6 hs | >6-12 hs | >12-24 hs | Baseline | 0.5-6 hs | >6-12 hs | >12-24 hs |
| 10 ng/ml | 116 ± 10 | 121 ± 11 | 125 ± 10 | 118 ± 10 | 61 ± 8 | 64 ± 8 | 65 ± 7 | 62 ± 7 |
| 20 ng/ml | 124 ± 21 | 116 ± 17 | 118 ± 20 | 116 ± 21 | 71 ± 12 | 66 ± 6 | 67 ± 6 | 64 ± 6 |
| BP ≤ 105 mmHg | 97 ± 8 | 106 ± 17 | 113 ± 25 | 109 ± 20 | 57 ± 6 | 61 ± 7 | 64 ± 8 | 62 ± 6 |

Figure 5A:
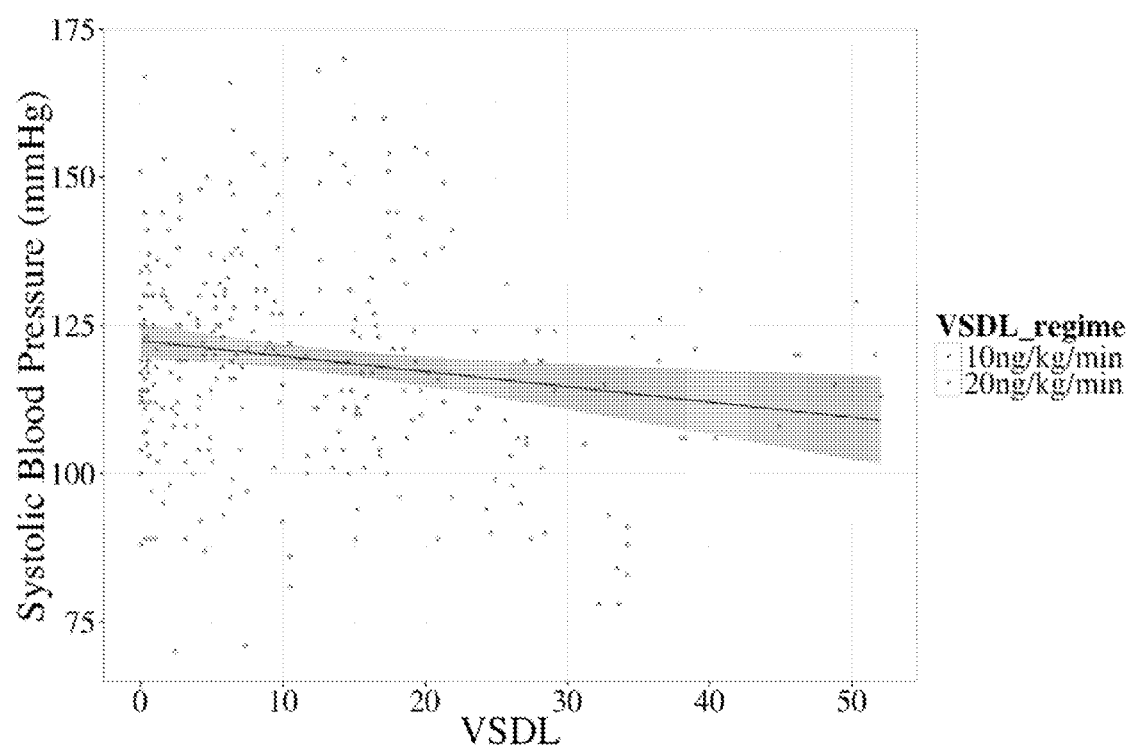
FIGS. 5A and 5B show a plot of blood pressure effects relative to VSDL concentration.
Figure 5B:
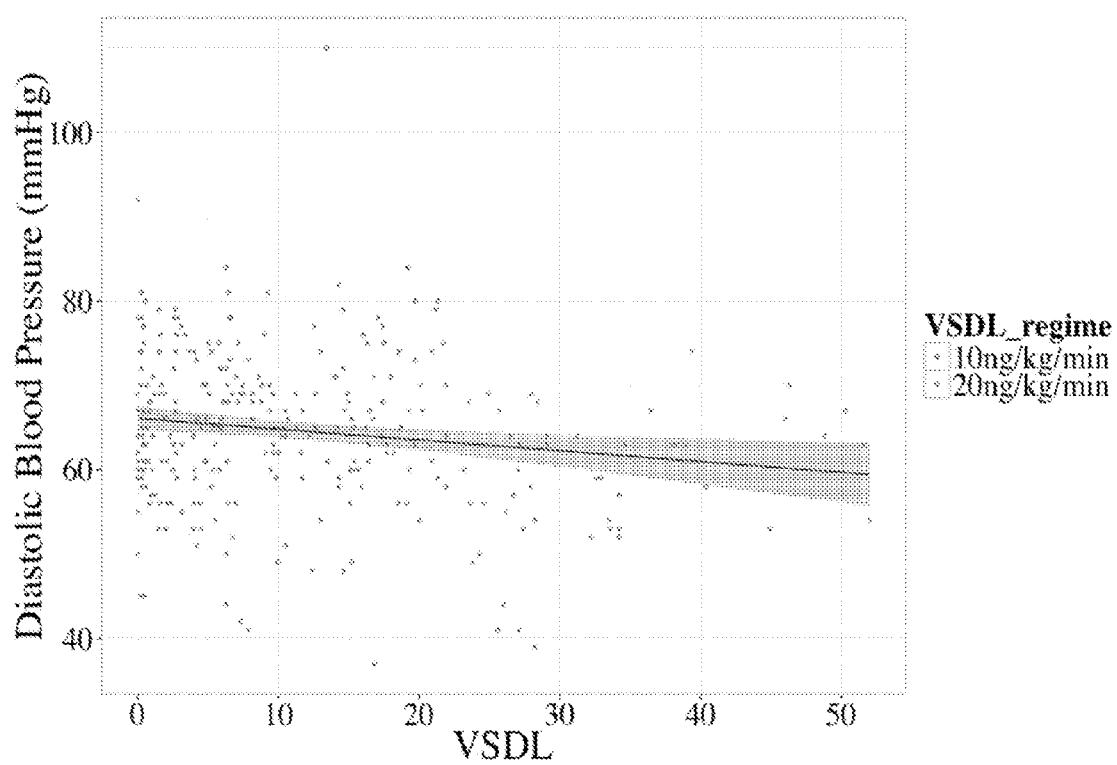

In order to demonstrate the blood pressure effects relative to VSDL concentration, the analysis was repeated using regression of systolic blood pressure on concentration of VSDL accommodating repeated measures, and these results demonstrated that, at higher concentrations, patients treated with VSDL had a significant decrease in systolic and diastolic blood pressures (p=0.005)(FIGS. 5A and B). However, there were no severe adverse events reported and all reported adverse events were self-limiting, recovering without need for intervention.

Effects of VSDL on Cardiovascular Haemodynamics

Regression of cardiac output on time accommodating repeated measures demonstrated that patients treated with VSDL had an increase in cardiac output equating to an increase on average of 0.000472 L/min above baseline (t=3.16; p≤0.05). The changes in cardiac output in 6 hour intervals post infusion are shown in Table 5. The infusion of VSDL resulted in numerical decreases in systemic vascular resistance (baseline=3076+929; ≥0.5-6 hs=2658+676; ≥6-12 hs=2529+509; ≥12-24 hs=2485+645 dyn·s/cm$^5$), but there were no changes to pulmonary vascular resistance. Moreover, in the limited patient numbers to date, adjuvant VSDL treatment has resulted in either decreased or unchanged pulmonary capillary wedge pressure.

TABLE 5

Cardiac haemodynamics of VSDL
Cardiac Output (L/min)

| Time Points | Baseline | >0.5-6 hrs | >6-12 hrs | >12-24 hrs |
|---|---|---|---|---|
| Mean | 4.7 | 4.6 | 4.9 | 5.0 |
| Median | 4.7 | 4.2 | 4.3 | 4.4 |
| Standard Deviation | 1.3 | 1.2 | 1.3 | 1.2 |
| Min/Max | 3.2/6.9 | 3.4/6.9 | 3.8/7.5 | 3.7/7.3 |

VSDL Enhances Urine Output Via Increased Sodium Excretion

Figure 2:
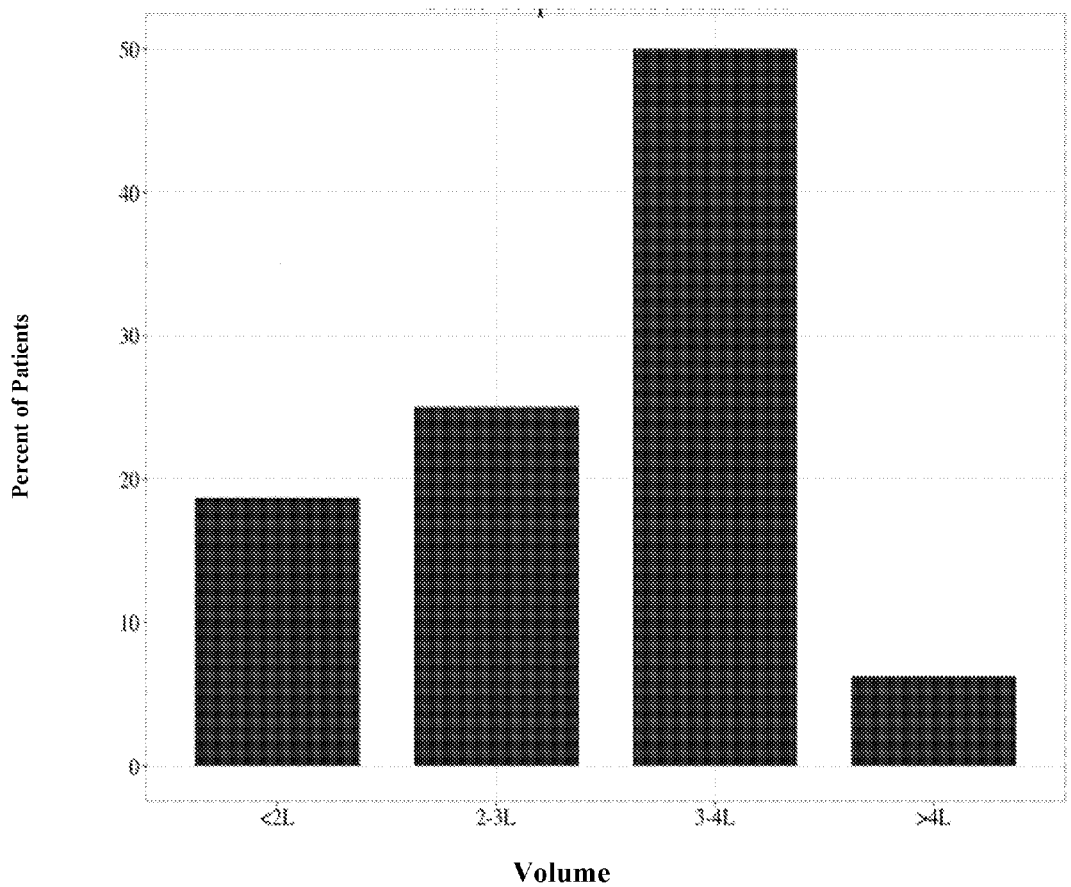
FIG. 2 shows a plot of urine output (L) vs percent of patients treated to achieve a Css of VSDL of 10 ng/ml or 20 ng/ml. The left hand column (<2 L) is the baseline result achieved with SOC treatment. The other columns represent pooled results (based on urine output) of the VSDL-treated patients.
Figure 3:
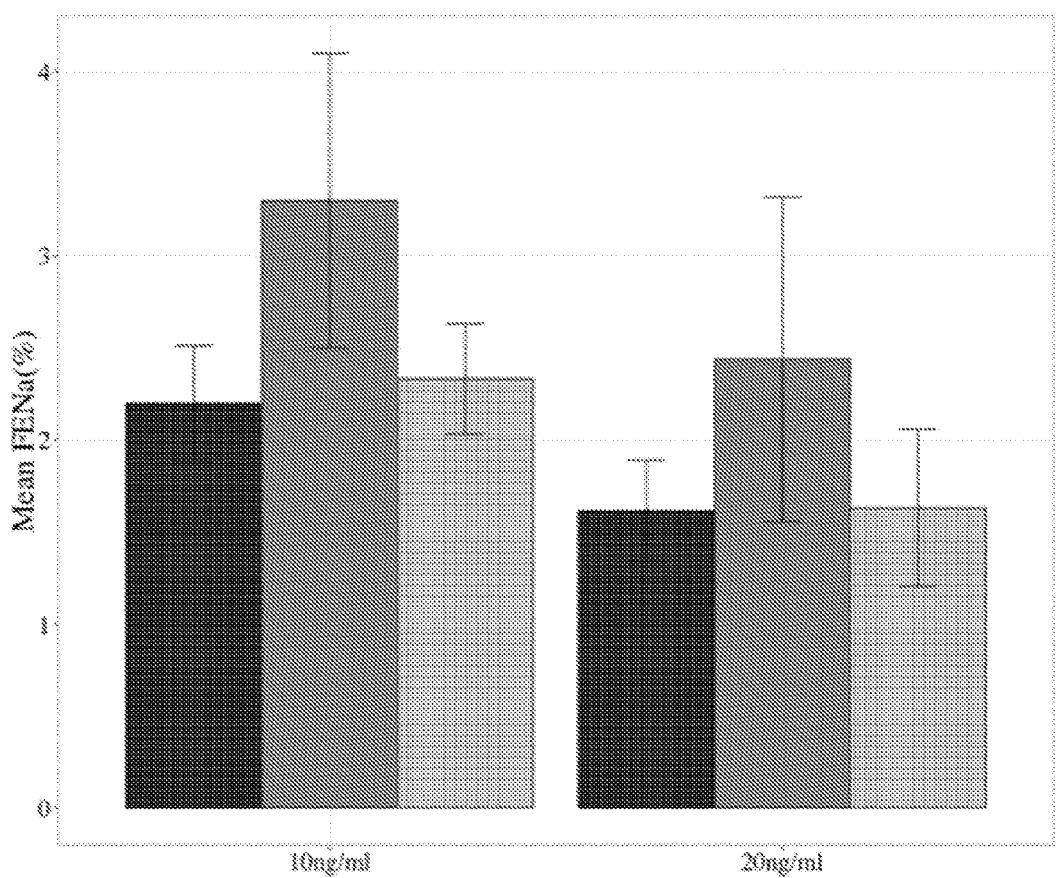
FIG. 3 shows a plot mean of Fractional Excretion of Sodium (FENa) (%) for stable CHF patients treated to achieve a Css of VSDL of 10 ng/ml or 20 ng/ml.

Patients treated with VSDL had increased fluid output as evidenced by increased urine volumes from baseline. The mean urine outputs were 2898±334 ml and 3028±301 ml in the 10 and 20 ng/ml cohorts respectively. Remarkably, more than 50% of the patients had urine volumes above 3 liters/day (FIG. 2). Although not statistically significant, in the 10 ng/ml cohort, $FE_{Na}$ increased from 2.2±0.3% at baseline to 3.3±0.8% during infusion and 2.3±0.3% post infusion. In the 20 ng/ml cohort, during infusion $FE_N$, increased to 2.4±0.8% from a baseline of 1.6±0.3% and returned to 1.6±0.4% post infusion (FIG. 3). These results confirm the results achieved in Example 1 indicating that increased sodium excretion is coupled with increased urine output in patients treated with VSDL.

VSDL Improves Renal Function

Figure 4:
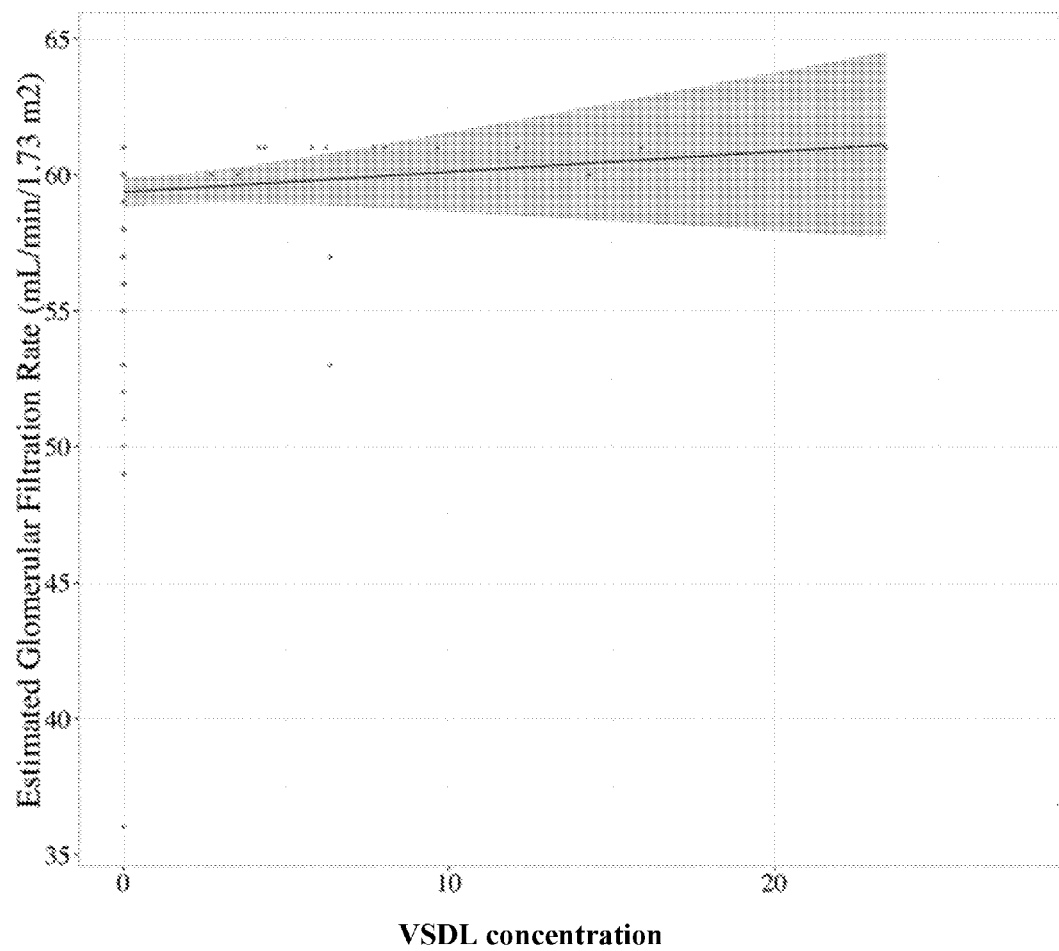
FIG. 4 shows a plot of blood plasma VSDL concentration (ng/ml) vs estimated glomerular filtration rate (mL/min/1.73 $m^2$) for stable CHF patients treated to achieve a Css of VSDL of 20 ng/ml.
Figure 6A:
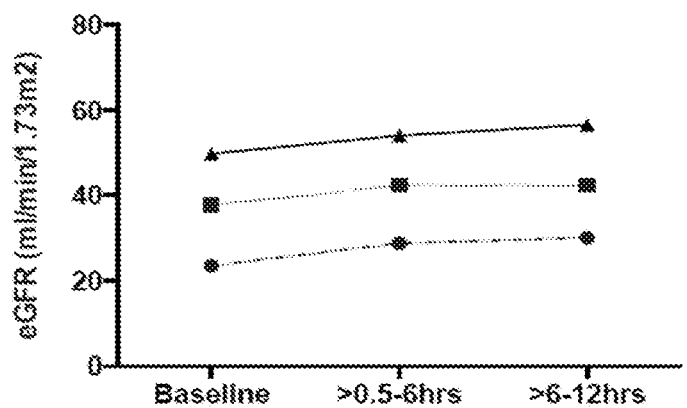
FIGS. 6A and 6B provide graphical results showing positive effects on renal function: both eGFR (FIG. 6A) and plasma creatinine levels (FIG. 6B) improved with rising circulating levels of VSDL
Figure 6B:
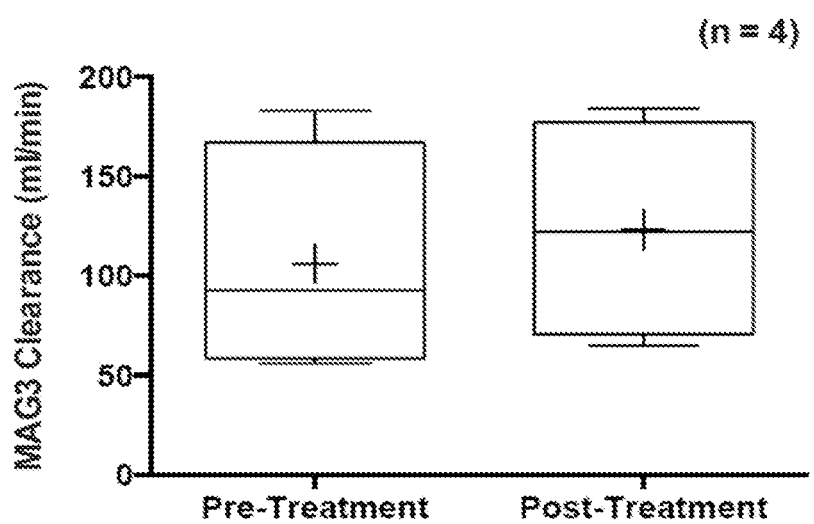

Adjuvant treatment with VSDL resulted in a significant improvement in estimated glomerular filtration rate (eGFR) from 38±11 ml/min/1.73 m$^2$ at baseline to 44±14 ml/min/1.73 m$^2$ (p≤0.05) during the 12 hour infusion of VSDL; which represents a 16% improvement in eGFR in these patients (FIG. 4). This change was also accompanied by a 10% decrease in plasma creatinine from 162±58 μmol/L at baseline to 146±60 mol/L (p≤0.05) during infusion (Table 6). These results were also confirmed using technetium-99m mercaptoacetyltriglycine (MAG3) as an additional measure of renal blood flow plus renal function; these analyses clearly indicating that MAG3 clearance was also improved in the VSDL treated patients (ie MAG3 clearance increased from 140±44 ml/min/1.73 m$^1$ pre-treatment to 149±41 ml/min/1.73 m$^2$ post-treatment (p≤0.05) (Table 6)). Moreover, in order to ascertain that the positive changes in renal function were due to VSDL, eGFR and plasma creatinine was assessed in relation to plasma concentration of VSDL and, as shown in FIGS. 6A and B, both of these parameters improved with rising circulating levels of VSDL, thereby confirming the association of VSDL and improved renal function.

In heart failure, it is especially important to identify drug response in patients with altered kidney function. Therefore, for analysis purposes, all patients were analysed based upon a standard chronic kidney disease (CKD) classification. The results of the analyses indicated that adjuvant treatment with VSDL resulted in numerical increases in eGFR and MAG3 clearance across all classes of CKD (Table 6). This is especially evident in patients with Stage 4 CKD with eGFR of 15-29 ml/min/1.73 m$^2$ where a 28% improvement was achieved during VSDL infusion. These results were also mirrored in MAG3 clearances (Table 6).

TABLE 6

VSDL sustains kidney function in patients with varying renal functionality

| Time Points | Baseline | >0.5-6 hs (% Change) | >6-12 hs (% Change) |
|---|---|---|---|
| eGFR 15-60 ml/min/1.73 m$^2$ | 37.9 ± 11 | 42.6 ± 13 (12) | 43.8 ± 14 (16) |
| eGFR 15-29 ml/min/1.73 m$^2$ (Stage 4 CKD) | 23.5 ± 5 | 28.8 ± 10 (23) | 30 ± 12 (28) |
| eGFR 30 to 44 ml/min/1.73 m$^2$ (Stage 3B CKD) | 37.7 ± 4 | 42.3 ± 10 (12) | 42.3 ± 10 (12) |
| eGFR 45-59 ml/min/1.73 m$^2$ (Stage 3A CKD) | 49.8 ± 3 | 54.0 ± 4 (8) | 56.6 ± 4 (14) |
| Plasma Creatinine (μmol/L) | 161.7 ± 58 | 148.5 ± 60 (8) | 146 ± 60 (10) |

| | Pre-Treatment | Post-Treatment | Post (Pre-Treatment) |
|---|---|---|---|
| MAG3 Clearance (ml/min/1.73 m$^2$) | 140.3 ± 44 | 148.9 ± 41 (6) | 9 ± 12 |
| MAG3 Clearance (ml/min/1.73 m$^2$) (Stage 4 CKD) | 106.0 ± 58 | 123.3 ± 56 (16) | 17 ± 16 |
| MAG3 Clearance (ml/min/1.73 m$^2$) (Stage 3B CKD) | 164.5 ± 32 | 164.8 ± 33 (0) | .3 ± 9 |
| MAG3 Clearance (ml/min/1.73 m$^2$) (Stage 3A CKD) | 148.5 ± 26 | 162.5 ± 24 (9) | 14 ± 7 |

Results for Lead-in Patients

Although the targeted plasma concentration for the cohort LEAD-IN patients was 10 ng/ml, they were not included in the analyses mentioned above since the sc infusions of VSDL were performed at 900 μg/hr for 6 hours and not for 12 hours as with all other patients. The results obtained with these patients indicated that, like the patients of cohorts 1 and 2, there was no significant change in blood pressure (ie demonstrated by mean systolic blood pressures of 114±6 mmHg and mean diastolic blood pressure of 66±3 mmHg up to 24 hours post infusion). Moreover, similar to the cohort 1 and 2 patients, there was a trend in the lead-in patient s of improved renal function as evidenced by an improvement in eGFR and MAG3 clearance accompanied by decreases in the amount of plasma creatinine.

Discussion

Renal dysfunction often accompanies heart failure and, in fact, renal impairment is an independent risk factor of morbidity and mortality in patients with CHF (Hillege et al., 2000). Moreover irrespective of cardiac status of patient, CKD in and of itself often leads to progression of cardiovascular disease (Schrier, 2006). In this example, it was found that in patients with stable CHF (LVEF≤45%) and moderate renal impairment (eGFR of 25-70 mL/min/1.73 m$^2$), VSDL improved renal function and increased urine output with a mild increase in cardiac output when added to standard of care (SOC) treatment. It is considered that these positive renal effects places VSDL in a unique class of drugs that could be used for the treatment of CHF and ADCHF patients, including those with renal impairment (especially bearing in mind that present therapies for CHF often result in a significant reduction in renal function).

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

1. Aroll B, Doughty R, Andersen V. *British Medical Journal* 341:c3657 (2010).
2. Bathgate R, Halls M, van der Westhuizen E, Callander G, Kocan M et al., *Physiol Rev* 93:405-480 (2013).
3. Dickey D M, Burnett J C, Potter L R, *J Biol Chem* 283(50):35003-35009 (2008).
4. Dorland W. Dorland's pocket medical dictionary. *Elsevier Saunders*, 28$^{th}$ Edition (2009).
5. Ellison D H, *Semin Nephrol* 19(6):581-597 (1999).
6. Gottlieb S. www.cardioexchange.org/voices/nesiritide-does-not-increase-diuresis-in-adhf-patients (2013).
7. Guidelines for the prevention, detection and management of chronic heart failure in Australia. National Heart Foundation of Australia (October 2011).
8. Hillege H L, Girbes A R, de Kam P J, Boomsma F, de Zeeuw D, Charlesworth A, Hampton J R and van Veldhuisen D J. *Circulation* 102:203-210 (2000).
9. Kambayashi Y, Nakao K, Mukoyama M, Saito Y, Ogawa Y, Shiono S, Inouye K, Yoshida N and Imura H, *FEBS Lett* 259(2):341-345 (1990).
10. Kirshenbaum K, Zuckennann R N, Dill K A. *Curr Opin Struct Biol* 9: 530-535 (1999).
11. Lilly L S. Pathophysiology of heart disease. *Lippincott Williams & Wilkins*, 3$^{rd}$ Edition (2003).
12. O'Connor C M, Starling R C, Hernandez A F, Armstrong P W, Dickstein K et al., *New Engl J Med* 365(1):32-43 (2011).

13. Ronco C, McCullough S D, *Eur Heart J* 31(6):703-711 (2010).
14. Ruilope L M, Dukat A, Böhm M, Lacourcière Y, Gong J, Lefkowitz M P, *Lancet* 375:1255-1266 (2010).
15. Sahu P K, Pal A, Panda J, Patnaik S, *Indian J Pharmacol* 43(5):603-604 (2011).
16. Schrier R W. *J Am Coil Cardiol* 47:1-8 (2006).
17. Schubert-Zsilavecz M, Wurglics M. *Neue Arzneimittel* 2010/2011.
18. Teichman S, Unemori E, Dschietzig T, Conrad K, Voors A. et al., *Heart Fail Rev* 14:321-329 (2009).
19. Teichman S, Unemori E, Teerlink J, Cotter G, Metra M, *Curr Heart Fail Rep* 75:75-82 (2010).
20. Valente M A, Voors A A, Darmman K, Van Veldhuisen D J, Massie B M, O'Connor C M, Metra M, Ponikowski P, Teerlink J R, Cotter G, Davison B, Cleland J G, Givertz M M, Bloomfield D M, Fiuzat M, Dittrich H C and Hillege H L. *Eur Heart J* 35(19): 1284-1293 (2014).
21. Vesely D L, Norris J S, Walters J M, Jespersen R R, Baeyens D A. *Biochem Biophys Res Commun* 148:1540-1548 (1987).
22. Vesely D L, Douglass M A, Dietz J R, Gower W R, Jr., McCormick M T, Rodriguez-Paz G, Schocken D D. *Circulation.* 90:1129-1140 (1994).
23. Vesely D L, Dietz J R, Parks J R, Baig M, McCormick M T, Cintron G, Schocken D D. *Circulation.* 98:323-329 (1998).
24. Vesely D L, *Life* 53:153-159 (2002).
25. Vesely D L, *Am J Physiology* 285:F167-F177 (2003).
26. Voors A A, Dahlke M, Meyer S, Stepinska J, Gottlieb S. et al. *Circ Heart Failure* 7:994-1002, 2014).
27. Weber K T. *J Am Coll Cardiol* 44(6):1308-1310 (2004).
28. Wilcox C S, *J Am Soc Nephrol* 13(3):798-805 (2002).

The invention claimed is:

1. A method for treating and/or preventing cardio-renal syndrome (CRS) in a subject with a severely decreased estimated glomerular filtration rate (eGFR) in the range of 15-24 ml/min/1.73 m$^2$, comprising administering to the subject a diuretic agent in combination with vessel dilator (VSDL).

2. The method of claim 1, wherein the subject shows diuretic resistance or refractory diuretic responsiveness.

3. The method of claim 1, wherein the diuretic agent is a loop diuretic and/or potassium-sparing diuretic.

4. The method of claim 1, wherein the diuretic agent is furosemide, spironolactone or a combination thereof.

5. The method of claim 1, wherein the administration of the diuretic agent comprises standard of care (SOC) treatment for the cardio-renal syndrome.

6. The method of claim 1, wherein the diuretic agent is furosemide and the method comprises administering the furosemide and the VSDL in combination with an ACE inhibitor.

7. The method of claim 6, further comprising administering a vasodilator agent.

8. The method of claim 7, wherein the vasodilator agent is relaxin.

9. The method of claim 7, wherein the vasodilator agent is an angiotensin receptor blocker (ARB).

10. The method of claim 7, further comprising administering a neprilysin (NEP) inhibitor.

11. The method of claim 10, wherein the NEP inhibitor is sacubitril.

12. The method of claim 7, further comprising administering an agent selected from CXL-1427 or TRV027.

13. The method of claim 6, further comprising administering an adenosine A1 receptor antagonist.

* * * * *